(12) United States Patent
Broder et al.

(10) Patent No.: US 6,284,800 B1
(45) Date of Patent: Sep. 4, 2001

(54) METHODS AND COMPOSITIONS FOR TREATMENT OF ASTHMA

(75) Inventors: Samuel Broder, Weston; Tahir Ahmed, Coral Gables, both of FL (US)

(73) Assignee: Baker Norton Pharmaceuticals, Inc., Miami, FL (US)

( * ) Notice: Subject to any disclaimer, the term of this patent is extended or adjusted under 35 U.S.C. 154(b) by 0 days.

(21) Appl. No.: 09/042,344

(22) Filed: Mar. 13, 1998

Related U.S. Application Data

(60) Provisional application No. 60/040,745, filed on Mar. 13, 1997.

(51) Int. Cl.⁷ .......................... A61K 31/135; A61K 31/40
(52) U.S. Cl. .......................... 514/652; 514/411; 514/826
(58) Field of Search ........................... 514/411, 652, 514/826

(56) References Cited

PUBLICATIONS

CA 70:27435; Agosti et al., 1968.*
CA 101:204080, Tattersfield et al., 1984.*
CA 94:202424, Henry et al., 1981.*
Vogelmeier, C., et al , "Neutrophil proteinases and rhDNase therapy in cystic fibrosis", *Eur. Respir. J.*, 1996, 9, pp. 2193–2195.
Packer, Milton, et al. "The Effect of Carvedilol on Morbidity and Mortality in Patients with Chronic Heart Failure", *The New England Journal of Medicine*, vol. 334, May 23, 1996, No. 21, pp. 1349–1355.
Pfeffer, Marc A., et al. "β–Adrenergic Blockers and Survival in Heart Failure", *The New England Journal of Medicine*, vol. 334, May 23, 1996, No. 21, pp. 1396–1397.
Long, James W., *The Essential Guide to Prescription Drugs 1992*, HarperPerennial, pp. 900–905.
*The Pharmacologic Basis of Therapeutics, Fifth Edition*, Goodman, Louis S. and Alfred Gilman, MacMillan Publishing Co., Inc., 1975, pp. 425.
*The Pharmacologic Basis of Therapeutics, Fifth Edition*, Goodman, Louis S. and Alfred Gilman, MacMillan Publishing Co., Inc., 1975, pp. 547–552.
*The Merck Index, Eleventh Edition*, Merck & Co., Inc., 1989, pp. 1246.
*Physician's Desk Reference 52 Edition*, Medical Economics Company, Inc., 1998, pp. 2728–2730.

* cited by examiner

*Primary Examiner*—Russell Travers
(74) *Attorney, Agent, or Firm*—Simona Levi-Minzi

(57) ABSTRACT

The present invention comprises methods and compositions for the treatment of bronchorestrictive disorders, including asthma, in humans or animals. The methods and compositions are effective in treatment of inflammatory responses, such as those found in asthma and other related pathologies.

3 Claims, 19 Drawing Sheets

METHODS AND COMPOSITIONS FOR TREATMENT OF ASTHMA

CROSS-REFERENCE TO RELATED APPLICATIONS

This application claims priority to U.S. Provisional Application No. 60/040,745, filed Mar. 13, 1997.

TECHNICAL FIELD

The present invention relates to methods and compositions for the treatment of pathologies associated with asthma and inflammatory responses in a human or animal. In particular, the present invention comprises compositions and methods for the treatment of asthma by administration of pharmaceutical preparations including D-propranolol.

BACKGROUND OF THE INVENTION

More than ten million persons in the United States suffer from asthma and related inflammatory lung diseases. The numbers of persons with asthma is increasing both in the United States and worldwide. The morbidity associated with asthma makes asthma a major medical condition. Asthma is the most common chronic disease of childhood and the leading cause among chronic illnesses of school absences. Asthma in humans results in an estimated 27 million patient visits, 6 million lost workdays, and 90.5 million days of restricted activity per year. In addition to its morbidity, the mortality rate for asthma is growing worldwide. Additionally, asthma reactions are a growing problem for animals. In particular, the horse racing industry is affected by horses that suffer from asthmatic reactions.

Asthma is a lung disease characterized by a usually reversible airway obstruction, airway inflammation and increased airway responsiveness to stimuli. The airway obstruction in an asthma attack is thought to be due to the combination of bronchospasm of the smooth muscles of the bronchial tree, increased mucous section, edema of airway mucosa due to increased vascular permeability, cellular infiltration of the airway walls, and injury to airway epithelium.

Asthma may be triggered by a variety of causes such as allergic reactions, a secondary response to infections, industrial or occupational exposures, ingestion of certain chemicals or drugs, exercise, and vasculitis. Regardless of the trigger, many of the pathological features of asthma can be attributed to mast cell degranulation. Mast cells will degranulate in response to many conditions in addition to the classical IgE-antigen stimulation. Not wishing to be bound by the following theory, it is theorized that when the asthmatic, human or animal, inhales an allergenic substance, sensitized IgE antibodies trigger mast cell degranulation in the lung interstitium. The mast cell degranulation releases among other factors, histamine, bradykinin, and slow-reacting substance of anaphylaxis (SRS-A) which includes the leukotrienes C, D and E, prostaglandins including $PGF_2$, $PGF_{2\alpha}$, and $PGD_2$, and thromboxane $A_2$. The histamine then attaches to receptor sites in the larger bronchi, causing irritation, inflammation and edema. The SRS-A attaches to receptor sites in the smaller bronchi, causing edema and attracting prostaglandins, which enhance the effects of histamine in the lungs. With the help of the prostaglandins, histamine also stimulates excessive mucous secretion, further narrowing the bronchial lumen. When the asthmatic inhales, the narrowed bronchial lumen still expands slightly, allowing air to reach the alveoli. However, upon exertion to exhale, the increased thoracic pressure closes the bronchial lumen completely. Thus, in an asthma attack, air can enter, but not exit the lungs. Mucous then fills the lung bases, inhibiting alveolar ventilation. In an effort to compensate for lowered alveolar ventilation, blood is shunted to other alveoli. Without adequate compensation, hypoxia, and in extreme cases, respiratory acidosis may result.

In many cases, there are two phases to an allergic asthma attack, an early phase and a late phase which follows 4–6 hours after bronchial stimulation. The early phase includes the immediate inflammatory response including the reactions caused by the release of cellular mediators from mast cells. Late phase reactions develop over a period of hours and are characterized histologically by an early influx of polymorphonuclear leukocytes and fibrin deposition followed later by infiltration of eosinophils. Late phase reactions increase airway reactivity and lead to prolonged asthmatic exacerbations that may last from hours to days to months in some subjects. One of the residual effects of asthma reactions is this hyperresponsiveness of the airways to nonspecific stimuli.

The current treatments for asthma are not adequate and many have serious side effects. The general goals of drug therapy for asthma are prevention of bronchospasm and control of airway hyperreactivity or hyperresponsiveness, an indication of airway inflammation. One effective treatment is avoidance of all allergens that trigger an asthma attack. Though scrupulous housecleaning and air cleansing devices can lessen the exposures to allergens, it is very difficult to eliminate all exposures to allergens. Thus, most asthmatics are treated with pharmacological agents that have side effects.

Another common treatment regimen is administration of adrenergic agonists. These compounds mimic the physiological effects of the adrenal medullary hormones and neurotransmitters of the sympathetic nervous system. The ideal therapeutic target for asthma would be a compound that affected the $\beta_2$-receptors in the lung. $\beta_2$-receptors are found in the airway and their stimulation causes smooth muscle relaxation, increased chloride fluxes and reduced vascular permeability. These effects would be very useful in asthma therapy.

Many side effects result from treatment with adrenergic agonists because the adrenergic agonists are generally not selective for only the $\beta_2$-receptors, but also effect the $\alpha$-receptors and $\beta_1$-receptors. $\beta_1$-receptors are found in the heart and adrenergic stimulation also leads to cardiac stimulation, which is a serious side effect of treatment with adrenergic agonists. Additionally, many of these compounds are rapidly metabolized and have very short half-lives, and thus are not effective therapy for asthma or hyperresponsiveness reactions. $\beta_2$-adrenergic agonists can be used for treatment of bronchospasm, but have no effect on airway inflammation or bronchial hyperreactivity. In fact, chronic use of $\beta_2$-adrenergic agents alone, by down regulation of $\beta_2$-receptors, may worsen bronchial hyperreactivity.

Asthma may also be treated with methylxanthines, such as theophylline. There is substantial variability in the absorbance and clearance of theophylline among animals. Even in individuals, theophylline clearance is effected by many physiological situations such as infection, antibiotic use, cigarette use and diet. The side effects of theophylline are nervousness, nausea, vomiting, anorexia, abdominal discomfort and headache. It is difficult to reach an effective drug level that provides asthma control without triggering side effects.

Corticosteroids are used to treat asthma by reducing the inflammatory component. Because the latephase asthmatic response is poorly responsive to bronchodilators, corticosteroids are used to treat late-phase and airway hyperreactivity reactions. These agents have tremendous toxicity in children, including adrenal suppression and reduced bone density and growth. In all age groups, corticosteroids have numerous side effects and complications which impact major organ systems. Use of oral corticosteroids must be closely monitored and its use curtailed or halted as soon as possible.

Cromolyn, another well known asthma therapeutic, acts by stabilizing mast cells and reducing or preventing release of the cellular mediators. Thus, cromolyn is effective in stopping or reducing both the early and late phases of asthma inflammatory reactions. Cromolyn is only effective in preventing the onset of an asthma reaction if given prior to an asthma attack. Once the asthma reaction has begun, the mediators have been released and treatment with cromolyn would do nothing to relieve the bronchoconstriction and hyperresponsiveness. Thus, asthma patients would have to take cromolyn continuously to prevent future asthma attacks that may or may not occur.

Thus, there is a long felt need for methods and compositions that are capable of inhibiting and stopping an asthma attack and its associated conditions, which are easily administered, and which do not have the side effects of currently used therapies. A simple and efficacious method of treatment would be through the inhalation route. If an anti-asthma agent could be given by an oral route, the many aspects of the pathology discussed above could be treated easily. The optimal dosage could be distributed in a form that the patient could self-administer at the onset of an attack or to stop hyperresponsiveness of the airways.

SUMMARY OF THE PRESENT INVENTION

In accordance with the present invention, compositions and methods are provided that are effective in preventing asthma and related pathologies. These methods and compositions are effective against inflammatory reactions in humans or animals. These compositions are easily administered by an oral route and can be given in dosages that are safe and effective. The present invention provides a method of treating asthma and related pathologies by administering a composition comprising a compound with anti-oxidant properties in a dosage sufficient to inhibit asthma.

Accordingly, it is an object of the present invention to provide compositions and methods to inhibit asthma and related pathologies in a human or animal.

It is yet another object of the present invention to provide a composition of inhibiting asthma and related pathologies by oral or inhaled administration of the composition.

It is another object of the present invention to provide methods of treatment of asthma.

It is another object of the present invention to provide methods of treatment of pathologies mediated by asthma.

It is yet another object of the present invention to provide a treatment for inflammatory responses.

It is an object of the present invention to provide methods and compositions of treatment of antigen-induced asthma.

It is an object of the present invention to provide methods and compositions of treatment of bronchial hyperreactivity.

Still another object of the present invention is to provide methods and compositions that are effective in diminishing specific and non-specific bronchial hyperreactivity.

These and other objects, features and advantages of the present invention will become apparent after a review of the following detailed description of the disclosed embodiments and the appended claims.

DETAILED DESCRIPTION OF THE PREFERRED EMBODIMENT

Figure 1:
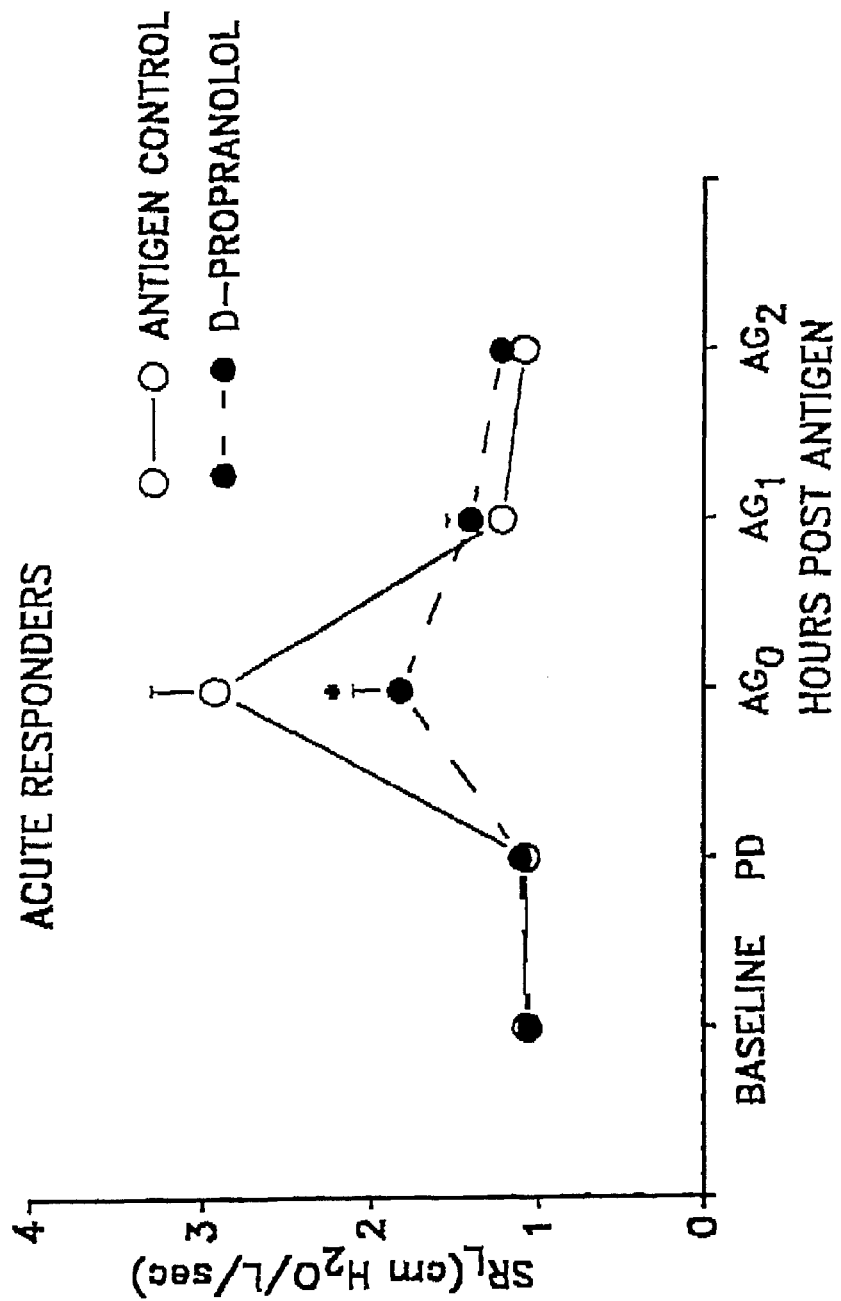
FIG. 1 is a graph showing the effect of D-propranolol in acute responder allergic sheep. Data are shown as mean±SE specific lung resistance ($SR_L$), for the baseline, after D-propranolol (PD) and for up to two hours post-antigen. D-propranolol was administered one hour before the antigen challenge (10 mg in 4 mL of PBS). * Significantly different from antigen control (P<0.05).

The present invention includes compositions and methods for the treatment of asthma and related pathologies. The present invention also includes compounds that may have antioxidant activity and in some cases, lack ability to block beta receptors in the human or animal. The present invention comprises methods of treating asthma in a human or animal comprising the steps of administering to the human or animal with the asthma, a composition comprising an effective amount of an antioxidant compound.

One embodiment of the present invention is the use of D-propranolol or the congeners of D-propranolol as disclosed herein to inhibit asthma and related pathologies. The optical isomer of D-propranolol is L-propranolol. L-propranolol is in the class of drugs that cause beta receptor blockade. β-adrenergic blocking agents have been used to treat such diverse diseases as glaucoma, migraine, hypertension, myocardial infarct and tremor. For example, L-propranolol is administered orally and is metabolically converted in the body by hepatic p450 enzymes to a metabolite that is effective for blocking beta receptors found in bodily tissues such as the heart and lung, in addition to other organs. Thus, L-propranolol is used to treat high blood pressure and certain forms of angina.

L-propranolol's sympathetic agonist or beta-blocker activity makes it an effective therapeutic for cardiac and hypertensive conditions, but this same activity creates adverse reactions for asthmatics. L-propranolol can precipitate asthma and in patients with severe asthma, the use of L-propranolol is contraindicated because serious or lethal asthmatic episodes of bronchoconstriction can occur.

The optical isomer of L-propranolol, D-propranolol, is thought to be biologically inactive. Thus, it is the surprising finding of the compositions and methods of the present invention that D-propranolol is effective therapy for asthma. D-propranolol is effective in the prevention of antigen-induced bronchoconstriction in sheep. The sheep model is a good animal model for the asthmatic condition in humans.

Though not wishing to be bound by any theory, it is theorized that D-propranolol, its metabolites and congeners and analogs play a role in stopping or inhibiting the inflammatory reactions mediated by mast cells and other inflammatory agents in asthma. Control of inflammatory reactions by D-propranolol, its metabolites and congeners and analogs make such compounds useful for treatment of other pathologies with inflammatory components. Diseases associated with chronic inflammation can be treated by the compositions and methods of the present invention. Diseases with symptoms of chronic inflammation include, but are not limited to, inflammatory bowel diseases such as Crohn's disease and ulcerative colitis, psoriasis, sarcoidosis and rheumatoid arthritis.

Again, though not wishing to be bound by any particular theory, it is theorized that the antioxidant activities of the compositions of the present invention aid in the compositions' effectiveness in treatment of asthma. An antioxidant is more readily oxidized than is a second substance and therefore, the antioxidant retards or inhibits the oxidation of the second substance. Treatment of other disease states in which control of oxidative activity is relevant is contemplated by the methods and compositions of the present invention.

The compounds and methods of the present invention may be used in treatment of cystic fibrosis. Cystic fibrosis is a genetic disease in which there is, among other pathologies, an overproduction of a thickened mucous and lack of digestive enzymes. Neutrophil elastase, released during an inflammatory response, is thought to play a central role in cystic fibrosis and in inflammatory disorders.

Neutrophil elastase is a serine protease that is stored in granules of mature neutrophils and functions in degradation of phagocytosed proteins. During neutrophil stimulation, neutrophil elastase and other enzymes gain access to the extracellular space where they cause substantial damage to the surrounding lung tissue, inhibit cell functions and inactivate molecules relevant to the integrity of the lung.

The lung is protected from neutrophil elastase and other such enzymes by several antiproteinases such as $\alpha_1$-proteinase inhibitor ($\alpha_1$-PI) and secretory leucoprotease inhibitor (SLPI). In a noninflamed lung, the activity of these antiproteinases functions to control proteinase activity and prevents proteinase damage to the lung. During neutrophil stimulation in an inflamed lung, in addition to proteinase release, stimulated neutrophils release reactive oxygen metabolites and the oxidative enzyme, myeloperoxidase. Not only are the reactive oxygen metabolites damaging to lung tissue, the protective antiproteinases are turned off by oxidative inactivation. Thus, compounds having antioxidative activity, such as those of the present invention, could function both in lung tissue protection and in preventing the inactivation of the protective enzymes.

There are numerous veterinary applications for the compositions and methods of the present invention. For example, the compounds included in the present invention can be used to treat asthmatic animals such as race horses. Additionally, animals also suffer with diseases due to inflammatory and oxidative reactions.

Compounds that can be used in accordance with the present invention include compounds that lack beta blocker activity. Additionally, compounds that can be used in accordance with the present invention include compounds that are capable of being acted on by the class of enzymes identified as p450 enzymes.

Examples of compounds included in the present invention comprise D-propranolol and its congeners, including fluorinated congeners and analogs. Additional examples include the appropriate optical isomer of carvedilol, metoprolol, bisoprolol and their metabolites and congeners and analogs.

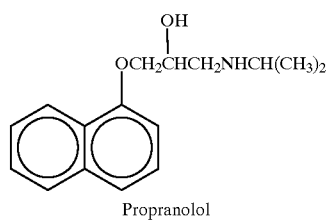

Propranolol

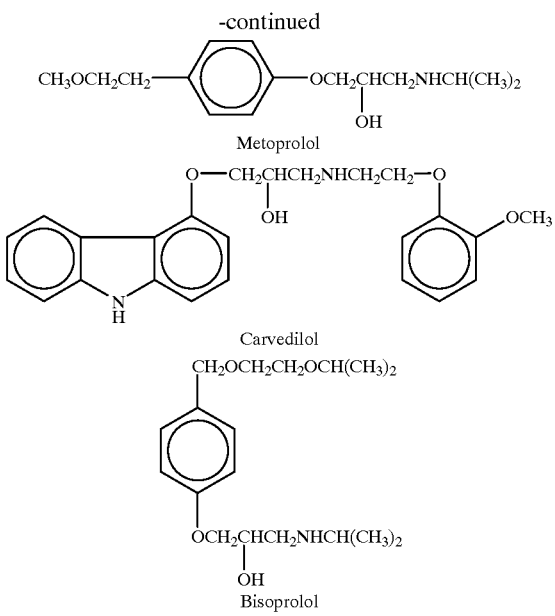

In summary, a preferred compound is D-propranolol as well as congeners, analogs, hydrolysis products, metabolites and precursors of D-propranolol and may lack beta receptor blocking capabilities. Such compounds may also have antioxidative activity. Other preferred compounds are the appropriate enantiomers or racemic mixture of bisoprolol, metoprolol, and carvedilol. It is envisioned that fluorinated congeners of all of these compounds are also useful for the present invention. However, it is to be understood that it is not necessary for a compound to have both a lack of beta receptor blocking activity and antioxidative activity to be considered part of the present invention. Such compounds as those acted upon by p450 enzymes are also contemplated by the present invention. It is to be understood that the compounds of the present invention can exist as enantiomers and that the racemic mixture of enantiomers or the isolated enantiomers are all considered as within the scope of the present invention.

The compounds described above can be provided as pharmaceutically acceptable formulations using formulation methods known to those of ordinary skill in the art. These formulations can be administered by standard routes. In general, the combinations may be administered by the topical, transdermal, oral, nasal, rectal or parenteral (e.g., intravenous, subcutaneous or intramuscular) route. In addition, the combinations may be incorporated into biodegradable polymers allowing for sustained release of the compound.

For inhalation formulations, the compounds of the present invention may be delivered via any inhalation methods known to those skilled in the art. Such inhalation methods and devices include, but are not limited to, metered dose inhalers with propellants such as CFC or HFA or propellants that are physiologically and environmentally acceptable. Other included devices are breath operated inhalers, multi-dose dry powder inhalers and aerosol nebulizers.

The dosage of the compound will depend on the condition being treated, the particular compound, and other clinical factors such as weight and condition of the human or animal and the route of administration of the compound. It is to be understood that the present invention has application for both human and veterinary use.

The formulations include those suitable for oral, inhalation, rectal, ophthalmic, (including intravitreal or intracameral) nasal, topical (including buccal and sublingual), vaginal or parenteral (including subcutaneous, intramuscular, intravenous, intradermal, intratracheal, and epidural) administration. The formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion and as a bolus, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated so as to provide a slow or controlled release of the active ingredient therein.

Formulation suitable for administration by inhalation includes formulations of the active ingredient in a form that can be dispensed by such inhalation devices known to those in the art. Such formulations may includes carriers such as powders and aerosols. The inhalant compositions used in the present invention may comprise liquid or powdered compositions containing the active ingredient that are suitable for nebulization and intrabronchial use, or aerosol compositions administered via an aerosol unit dispensing metered doses.

Suitable liquid compositions comprise the active ingredient in an aqueous, pharmaceutically acceptable inhalant solvent, e.g., isotonic saline or bacteriostatic water. The solutions are administered by means of a pump or squeeze-actuated nebulized spray dispenser, or by any other conventional means for causing or enabling the requisite dosage amount of the liquid composition to be inhaled into the patient's lungs.

Suitable powder compositions include, by way of illustration, powdered preparations of the active ingredient thoroughly intermixed with lactose or other inert powders acceptable for intrabronchial administration. The powder compositions can be administered via an aerosol dispenser or encased in a breakable capsule which may be inserted by the patient into a device that punctures the capsule and blows the powder out in a steady stream suitable for inhalation.

Aerosol formulations for use in the subject method would typically include propellants, surfactants and co-solvents and may be filled into conventional aerosol containers that are closed by a suitable metering valve.

Formulations suitable for topical administration in the mouth include lozenges comprising the ingredients in a flavored basis, usually sucrose and acacia or tragacanth;

pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. A preferred topical delivery system is a transdermal patch containing the ingredient to be administered.

Formulations for rectal administration may be prepared as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tamports, creams, gels, pastes, foams or spray formulations containing in addition to the active ingredient such carriers as are known in the art to be appropriate.

Formulations suitable for parenteral administration include aqueous and non-aqueous sterile injection solutions which may contain antioxidants, stabilizers, buffers, bacteriostats and solutes which render the formulation isotonic with the blood of the intended recipient; and aqueous and non-aqueous sterile suspensions which may include suspending agents and thickening agents. The formulations may be presented in unit-dose or multidose containers, for example, sealed ampoules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients, particularly mentioned above, the formulations of the present invention may include other agents conventional in the art having regard to the type of formulation in question, for example, those suitable for oral administration may include flavoring agents.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

D-propranolol was administered via the inhalation route as an aerosol one hour before antigen challenge in acute responder sheep. There was significant inhibition of allergic bronchoconstriction by the administered D-propranolol.

The following protocol is a well-known and art accepted animal model for measurement of antigen-induced asthmatic treatments.

Five allergic sheep, with previously documented acute bronchoconstrictor response to Ascaris suum antigen, were used for all studies. The sheep were intubated with a cuffed nasotracheal tube and pulmonary airflow resistance ($R_L$) was measured by the esophageal balloon catheter technique, while thoracic gas volume was measured by body plethysmography. Data was expressed as specific resistance, $SR_L$. $SR_L$ is defined as $R_L$ times thoracic gas volume ($V_{tg}$).

To assess the normal or baseline airway responsiveness of the sheep, cumulative dose response curves to inhaled carbochol were performed. The $SR_L$ of each sheep was measured before and after inhalation of a buffered saline solution and after each administration of 10 breaths of increasing concentrations of carbachol (0.25, 0.5, 1.0, 2.0 and 4.0% wt/vol solution). Airway responsiveness was defined by determination of the cumulative provocation dose ($PD_{400}$) of carbachol (in breath units) that increased $SR_L$ to 400% above baseline. One breath unit was defined as one breath of 1% carbachol solution.

FIG. 1 shows the effect of treatment using D-propranolol in an antigen challenge experiment. The normal reaction of the sheep to the antigen from Ascaris suum is measured. After full recovery and a two week rest period, the sheep again undergo repeat antigen challenge, but this time only after treatment with D-propranolol.

The $SR_L$ of the acute responder sheep was measured prior to any treatment (baseline). The normal response of the sheep to antigen challenge by Ascaris suum antigen was measured (Open circles). After appropriate recovery of at least two weeks, D-propranolol, 10 mg in 4 mL of PBS, (phosphate buffered saline), was administered as an aerosol one hour before antigen challenge in acute responder sheep and the $SR_L$ was measured (PD). One hour after D-propranolol was administered, the sheep were challenged with Ascaris suum antigen by inhalation. The $SR_L$ was measured immediately after antigen challenge ($AG_0$). As can be seen in FIG. 1, the sheep treated with D-propranolol (black circles) showed significantly less immediate allergic bronchoconstriction response to antigen challenge compared to the control, non-treated, sheep (open circles).

Figure 2:
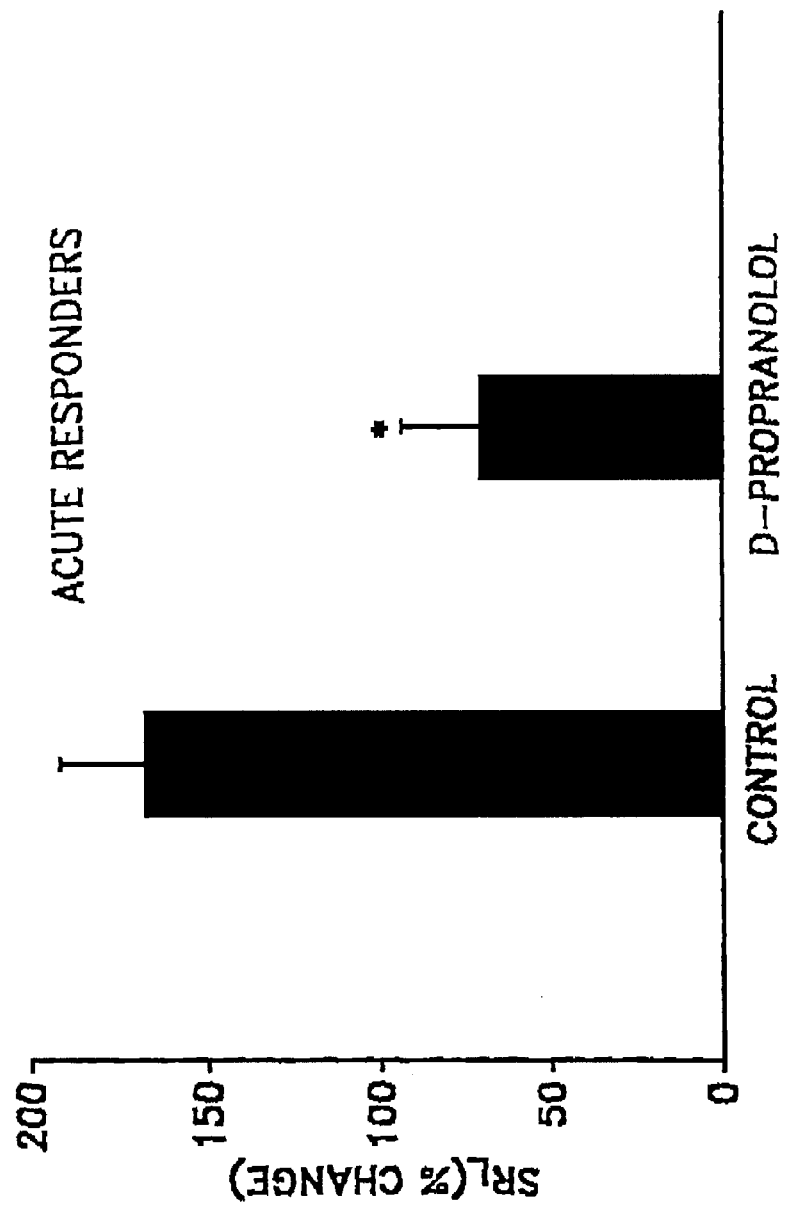
FIG. 2 is a graph showing the percentage of change in specific lung resistance ($SR_L$) in acute responder sheep after pretreatment with D-propranolol. Data shown are mean±SE % change in specific lung resistance ($SR_L$) (n=5). * Significantly different from antigen control (P<0.05).

FIG. 2 shows the percentage change in $SR_L$ for control conditions (normal response to Ascaris suum antigen) and treatment conditions (D-propranolol). When the sheep were treated with D-propranolol there was significantly less change in $SR_L$ after antigen stimulation than under the control conditions.

Figure 3:
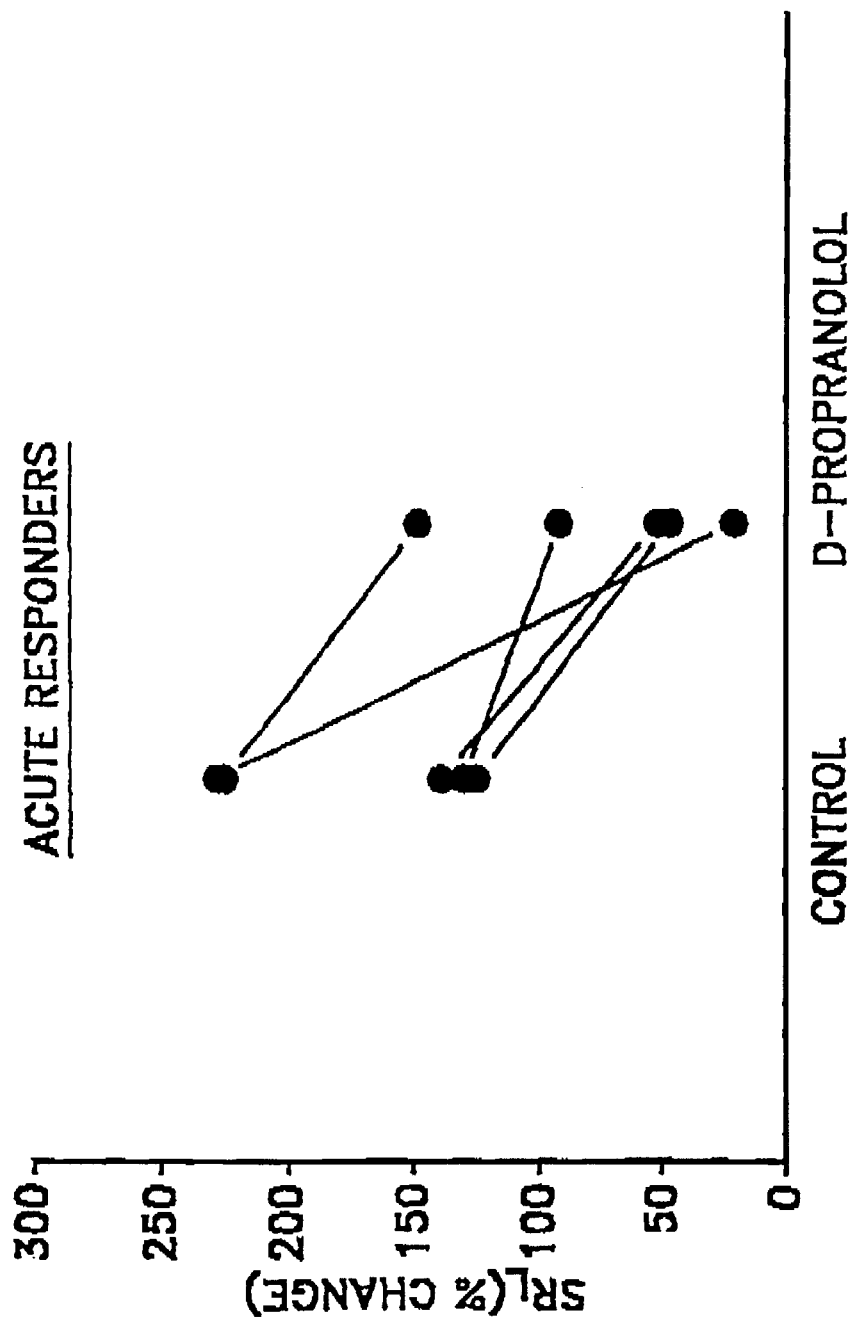
FIG. 3 is a graph showing the individual response of each sheep as percentage change in specific lung resistance ($SR_L$) after pretreatment with D-propranolol.

FIG. 3 shows the individual responses for the five sheep. As the graph shows, there was variability in the responses of the five sheep, but all sheep showed a difference in response to antigen after treatment with D-propranolol.

Figure 4:
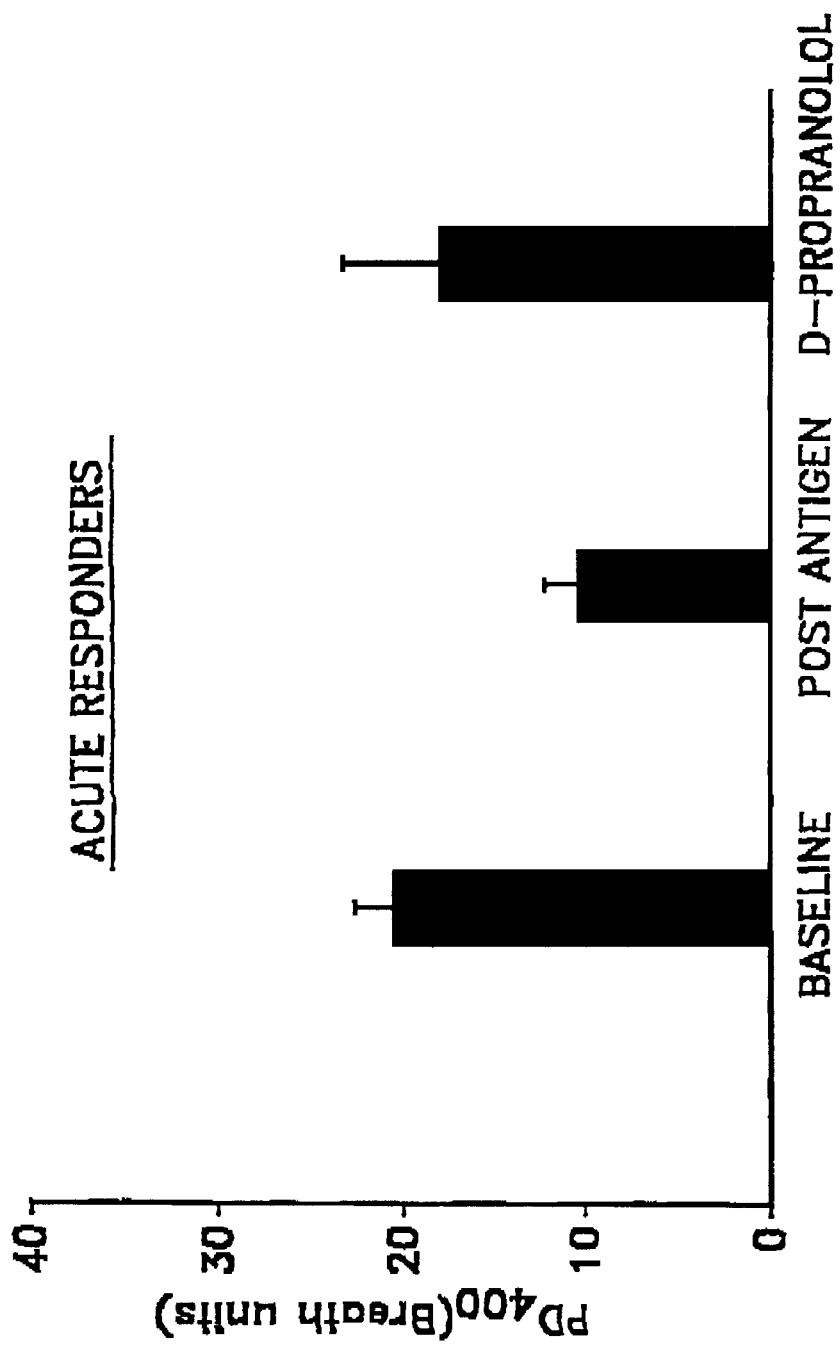
FIG. 4 is a graph showing the effect of pretreatment with inhaled D-propranolol (10 mg in 4 mL of PBS) on antigen-induced airway hyperresponsiveness. Data are shown as mean±SE $PD_{400}$ of carbachol in breath units (Cumulative provocating dose of carbachol, which increased $SR_L$ to 400% above the baseline). One breath unit is defined as one breath of 1% carbachol solution (P=NS).

FIG. 4 shows that treatment with D-propranolol maintains the sheep's airway responsiveness to antigen at or near baseline responsiveness levels. The effect of antigen on the sheep was to make the airway more responsive, thus lowering the $PD_{400}$ value. Treatment with D-propranolol maintained the airway responsiveness levels at the baseline or normal responsiveness levels of the sheep.

Figure 5:
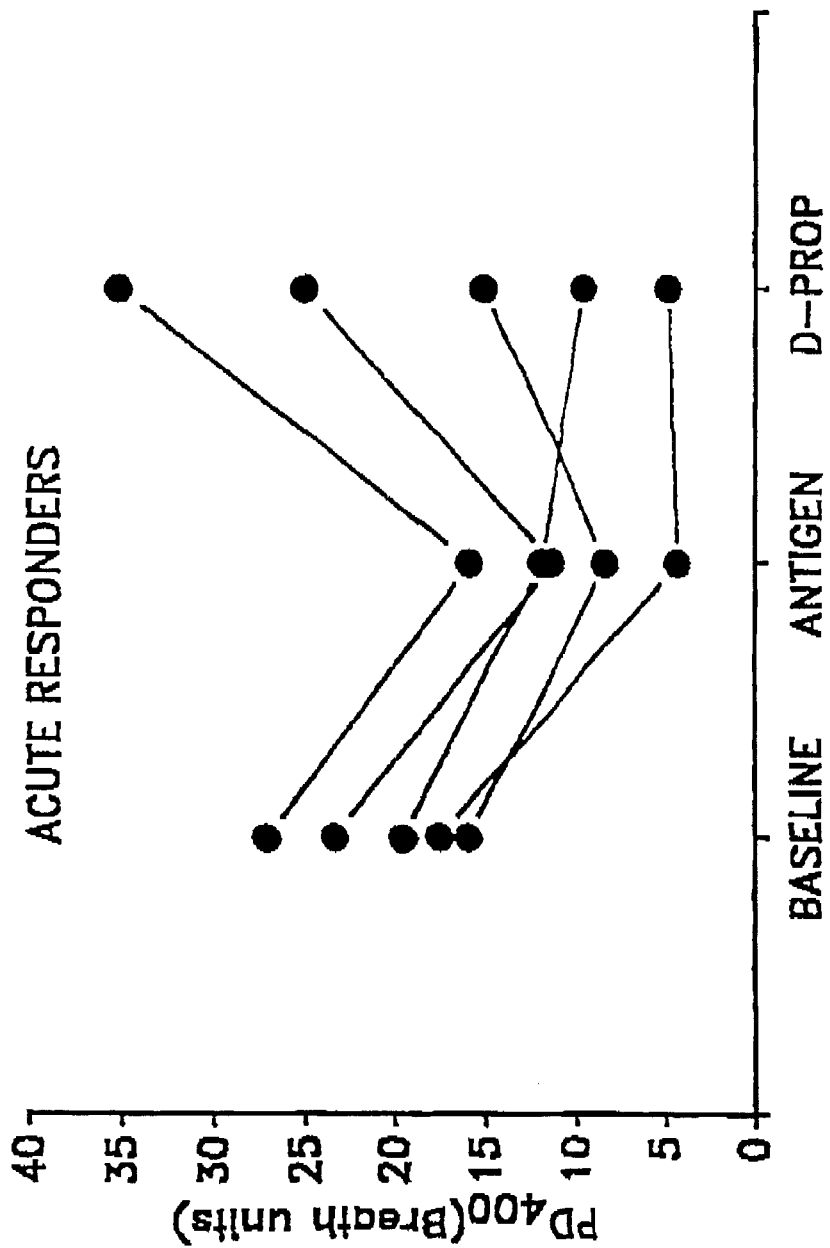
FIG. 5 is a graph showing the individual response of each sheep to the effect of pretreatment with inhaled D-propranolol on antigen-induced changes in $PD_{400}$.

FIG. 5 shows the individual airway responsiveness of each sheep to the treatment with D-propranolol. When challenged by antigen, each sheep showed a decreased $PD_{400}$. The effect of treatment with D-propranolol on airway responsiveness was different for each sheep.

As can be seen from these experiments, treatment with D-propranolol can attenuate an antigen-induced asthma attack.

EXAMPLE II

The comparative effects of L- and D-propranolol on antigen-induced bronchorestriction (ABR) and airway hyperresponsiveness (AHR) in sheep were tested. The sheep were treated as described in Example I. Propranolol, a nonselective beta-receptor antagonist is known to cause bronchorestrictions and worsen AHR.

Specific lung resistance ($SR_L$) was measured in 11 allergic sheep, of which six sheep were acute responders and five sheep were dual responders, before and serially after challenge with *Ascaris suum* antigen, without and after pretreatment with D- or L-propranolol. The propranolol was administered either in an inhaled dose or an oral dose.

Figure 6:
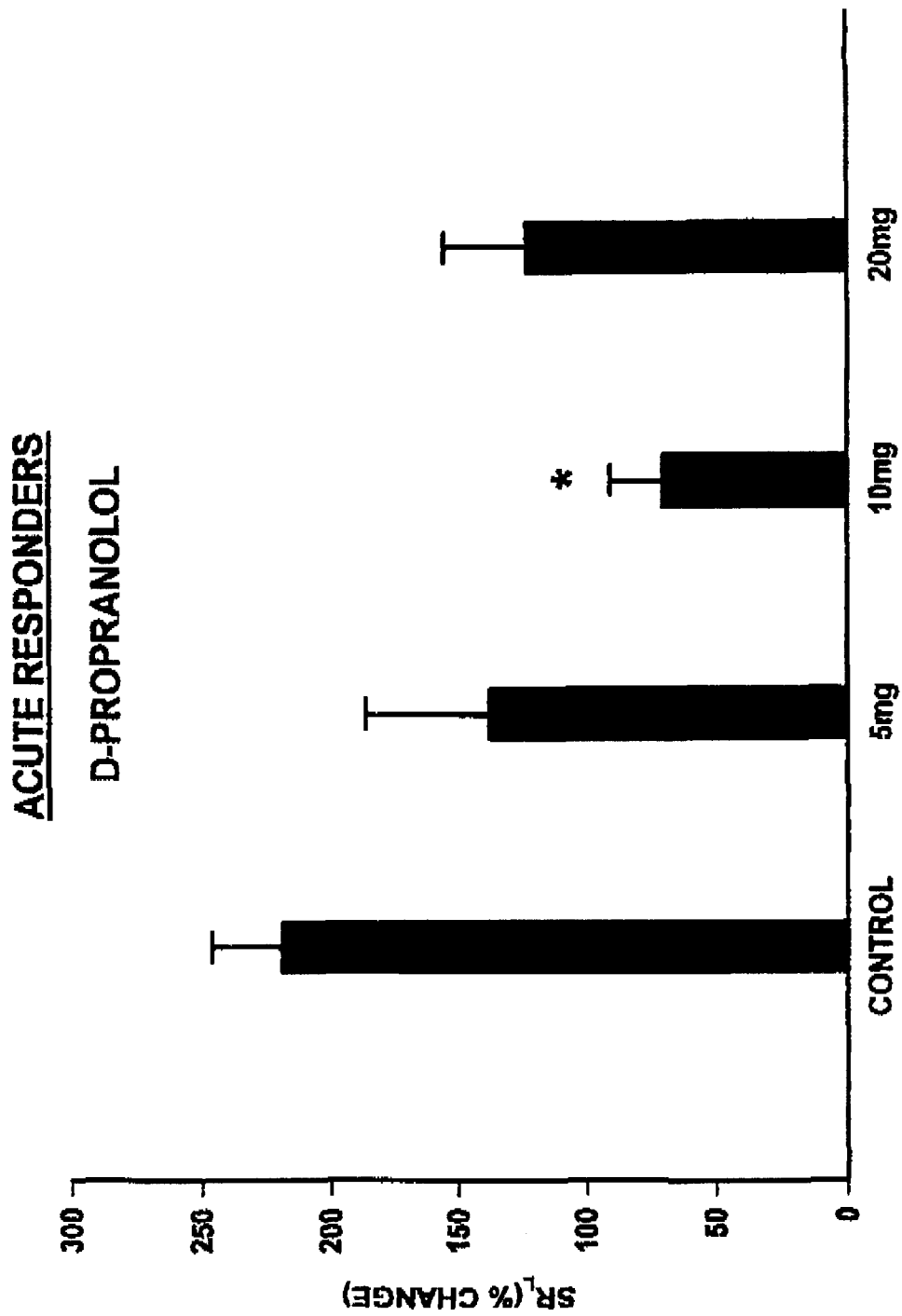
FIG. 6 is a graph showing the $SR_L$ response of acute responder sheep to different dosages of inhaled D-propranolol. The response at the 10 mg/kg dose is significantly different from the control.
Figure 7:
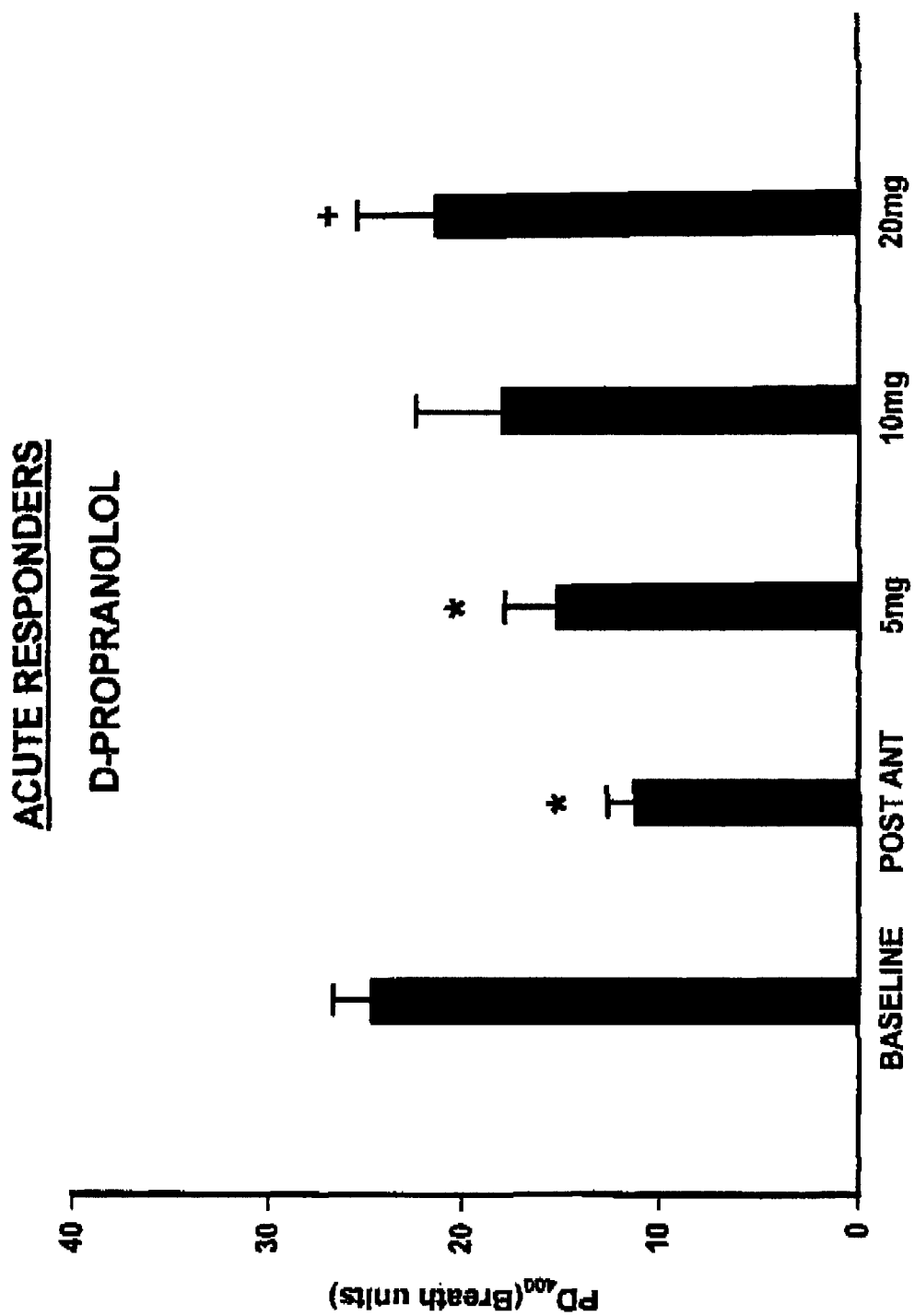
FIG. 7 is a graph showing the $PD_{400}$ response of acute responder sheep to different dosages of inhaled D-propranolol. The post antigen and 5 mg dose responses are significantly different from the baseline response, and the 20 mg dose response is significantly different from the post antigen response.

The following experiments used inhaled D- or L-propranolol. AHR was estimated at 2 hours (acute) or 24 hours (dual) after antigen challenge as the provoking dose of carbachol which increased $SR_L$ by 400% ($PD_{400}$). In acute responders, $SR_L$ increased by 219% with antigen challenge and $PD_{400}$ decreased by 55%. Inhaled D-propranolol had no effect on baseline $SR_L$, but inhibited ABR in a dose dependent manner. As shown in FIG. 6, ABR was inhibited by 37% at a 5 mg dose, by 68% at a 10 mg dose and 44% at a 20 mg dose. The 68% inhibition is significant, P<0.05. As shown in FIG. 7, AHR was inhibited by 30% at a 5 mg dose, 50% at a 10 mg dose, and 75% at a 20 mg dose. The 75% inhibition is significant, P<0.05, when compared to the post-antigen response. The 5 mg dose response is significantly different from the baseline response.

Figure 8:
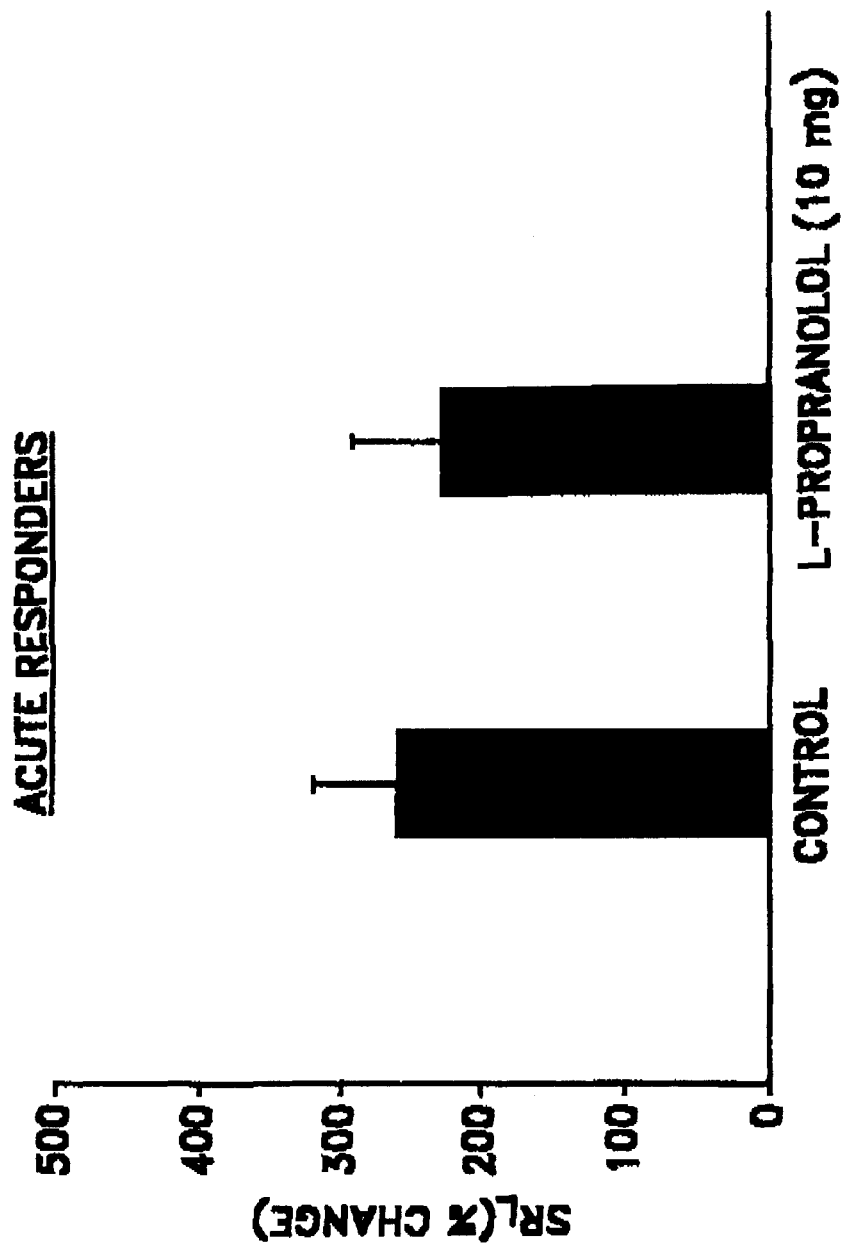
FIG. 8 is a graph showing the $SR_L$ response of acute responder sheep to a 10 mg dose of inhaled L-propranolol. There is no significant difference from the control response.
Figure 9:
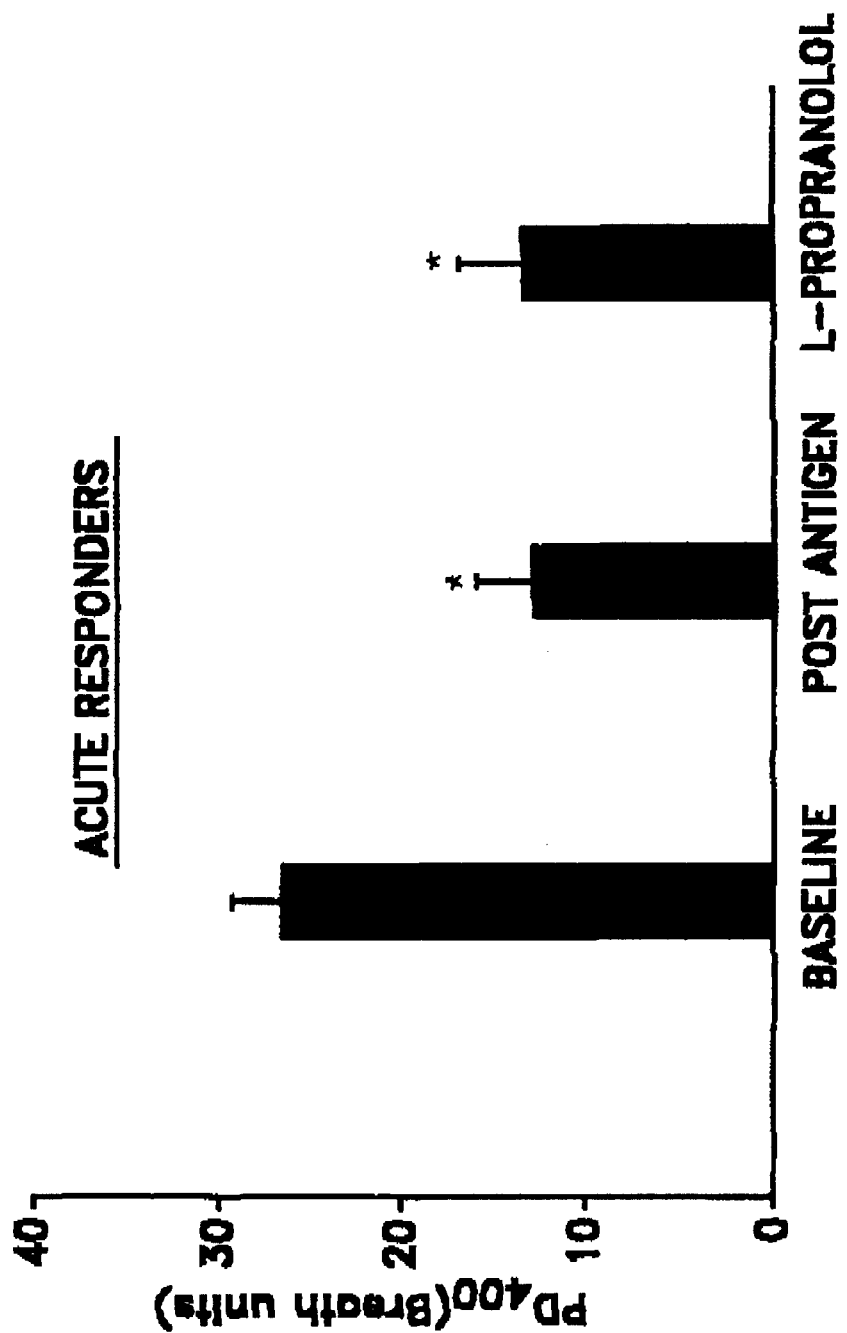
FIG. 9 is a graph showing the $PD_{400}$ response of acute responder sheep to a 10 mg dose of inhaled L-propranolol.

FIG. 8 shows that inhaled L-propranolol (10 mg dose) increased baseline $SR_L$, which resolved by 30 minutes, but had no effect on ABR, where the change in $SR_L$=209%. FIG. 9 shows the AHR response to inhaled L-propranolol where there is no difference between the post antigen and L-propranolol responses, though both are statistically different from the baseline response.

Figure 10:
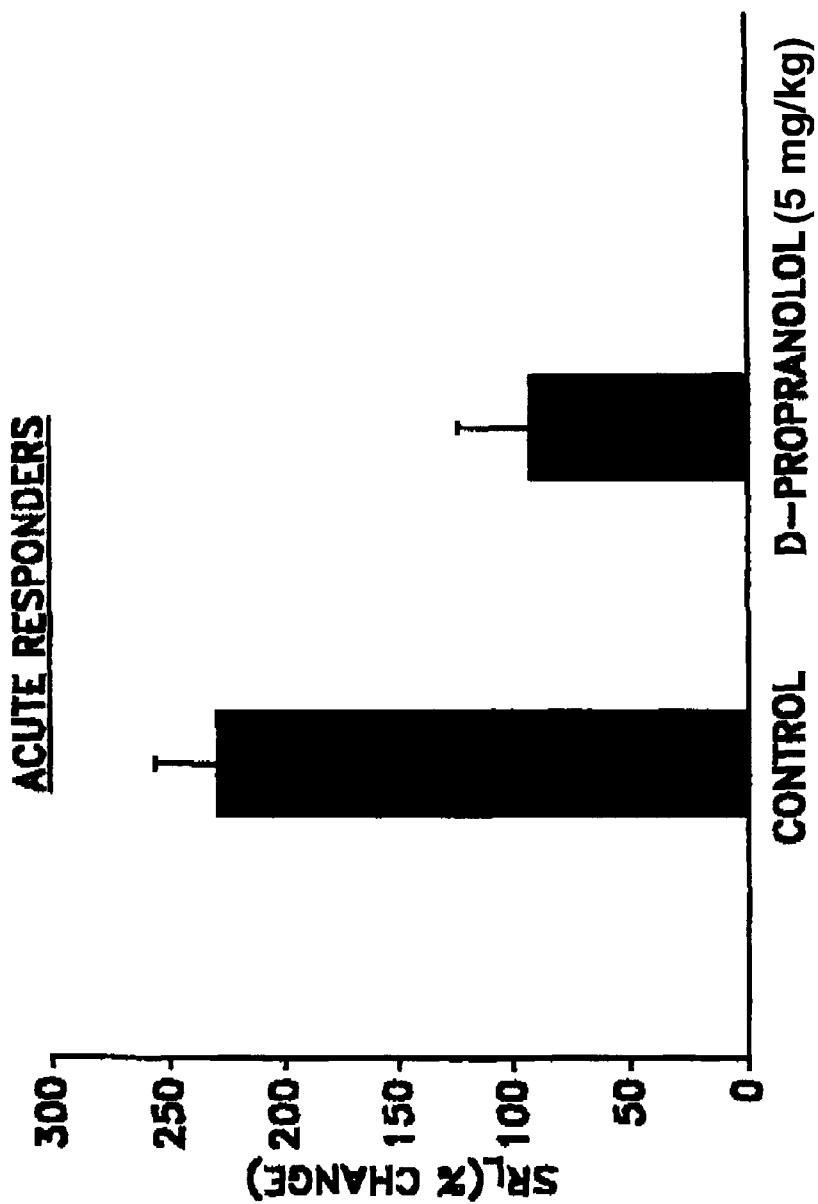
FIG. 10 is a graph showing the $SR_L$ response of acute responder sheep to a 5 mg/kg dose of oral D-propranolol.
Figure 11:
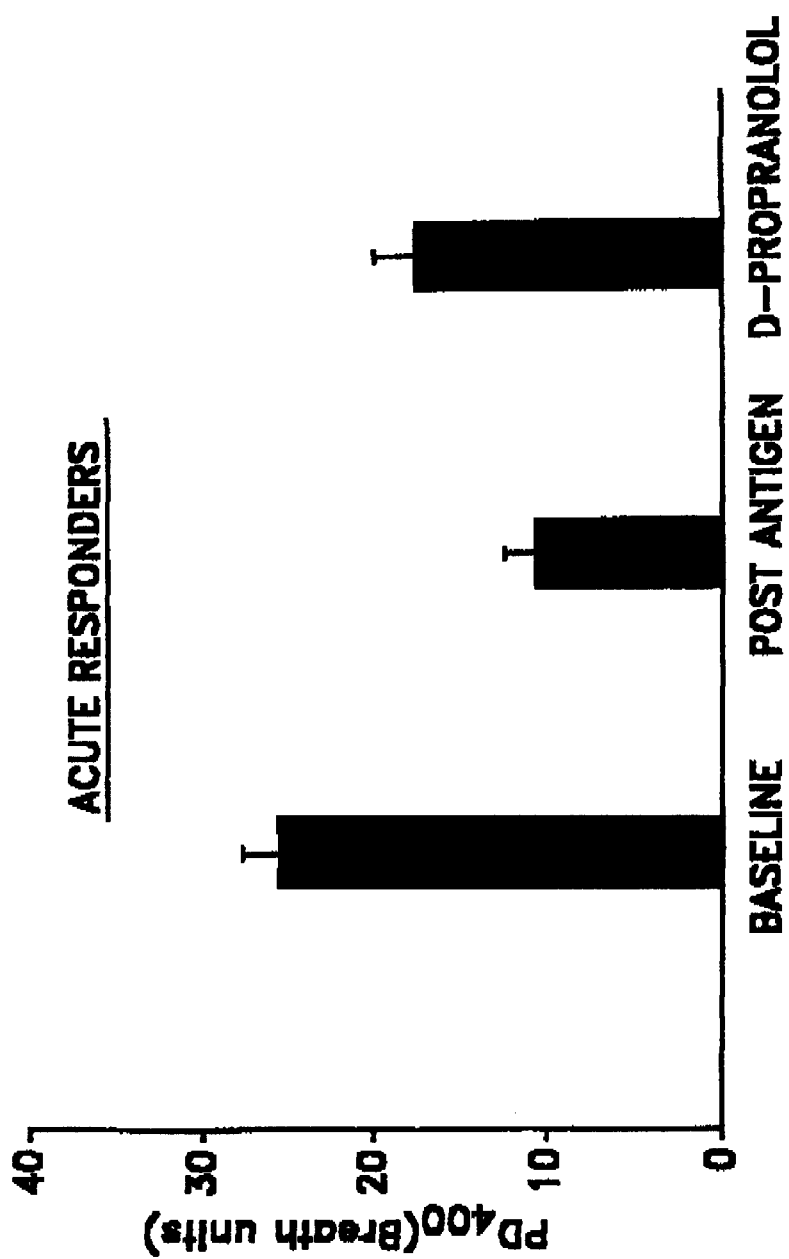
FIG. 11 is a graph showing the $PD_{400}$ response of acute responder sheep to a 5 mg/kg dose of oral D-propranolol.

Oral administration of D-propranolol also effects ABR and AHR responses. FIG. 10 shows the change in $SR_L$ to a 5 mg/kg dose of oral D-propranolol in acute responder sheep and FIG. 11 shows the change in $PD_{400}$ after oral administration of 5 mg/kg of D-propranolol.

Figure 12:
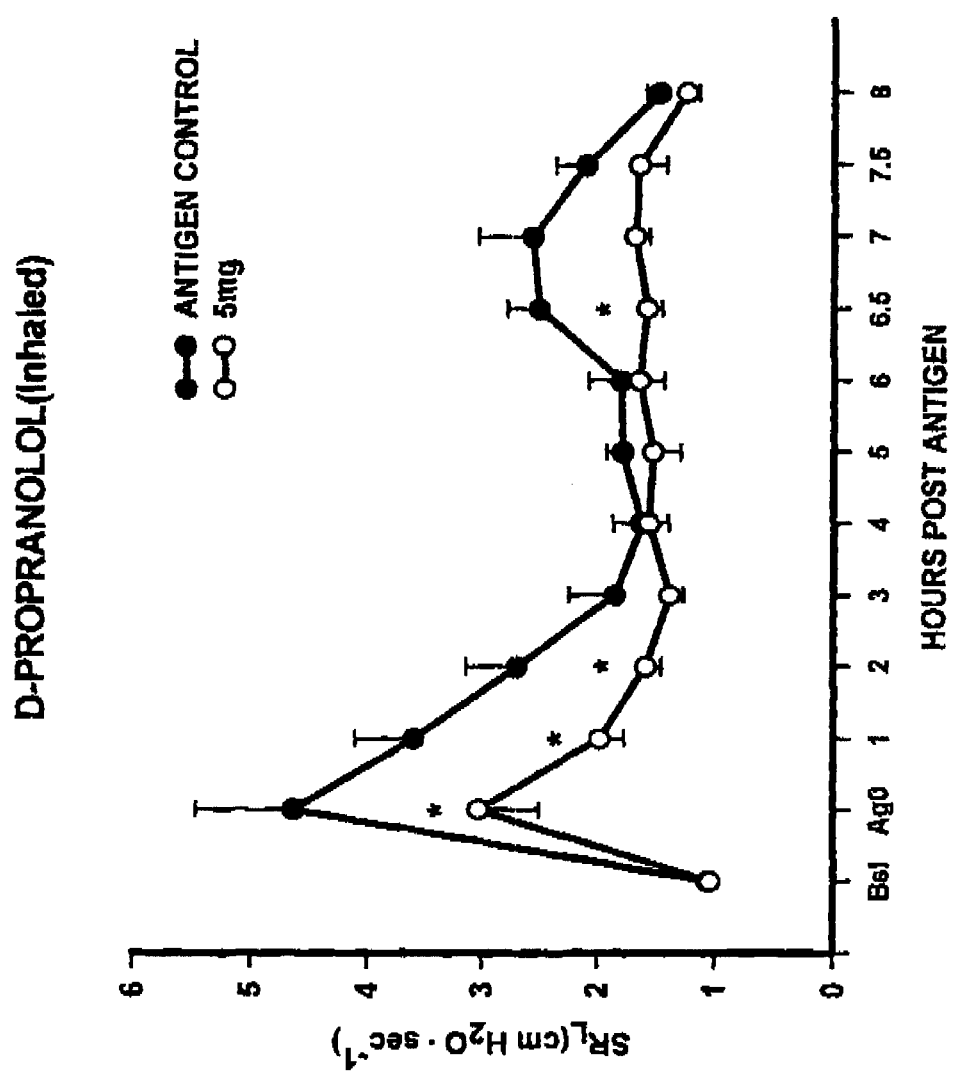
FIG. 12 is a chart showing the timeline of the $SR_L$ response of dual responder sheep to a 5 mg/kg dose of inhaled D-propranolol.
Figure 13:
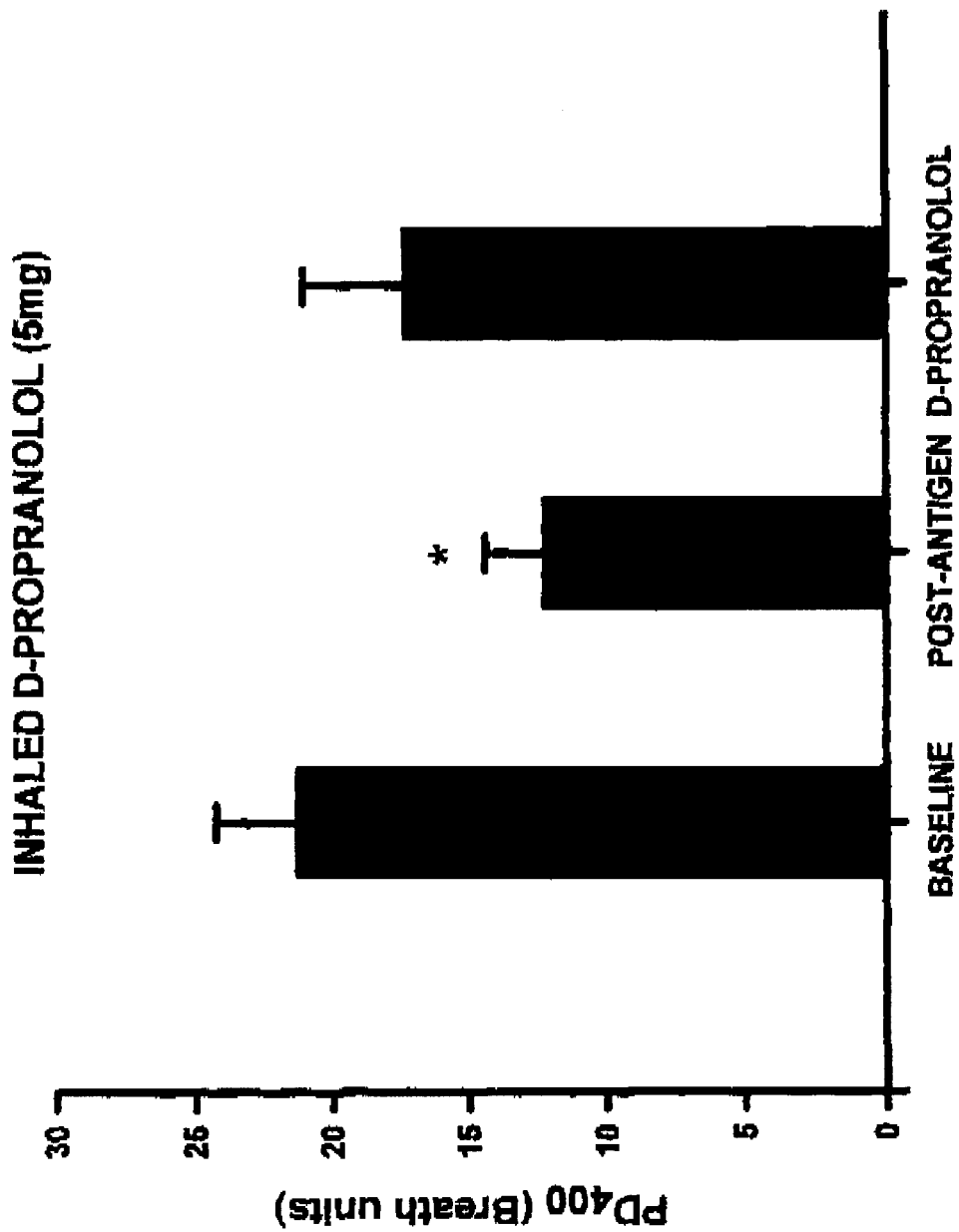
FIG. 13 is a graph showing the $PD_{400}$ response of dual responder sheep to a 5 mg/kg dose of inhaled D-propranolol.
Figure 14:
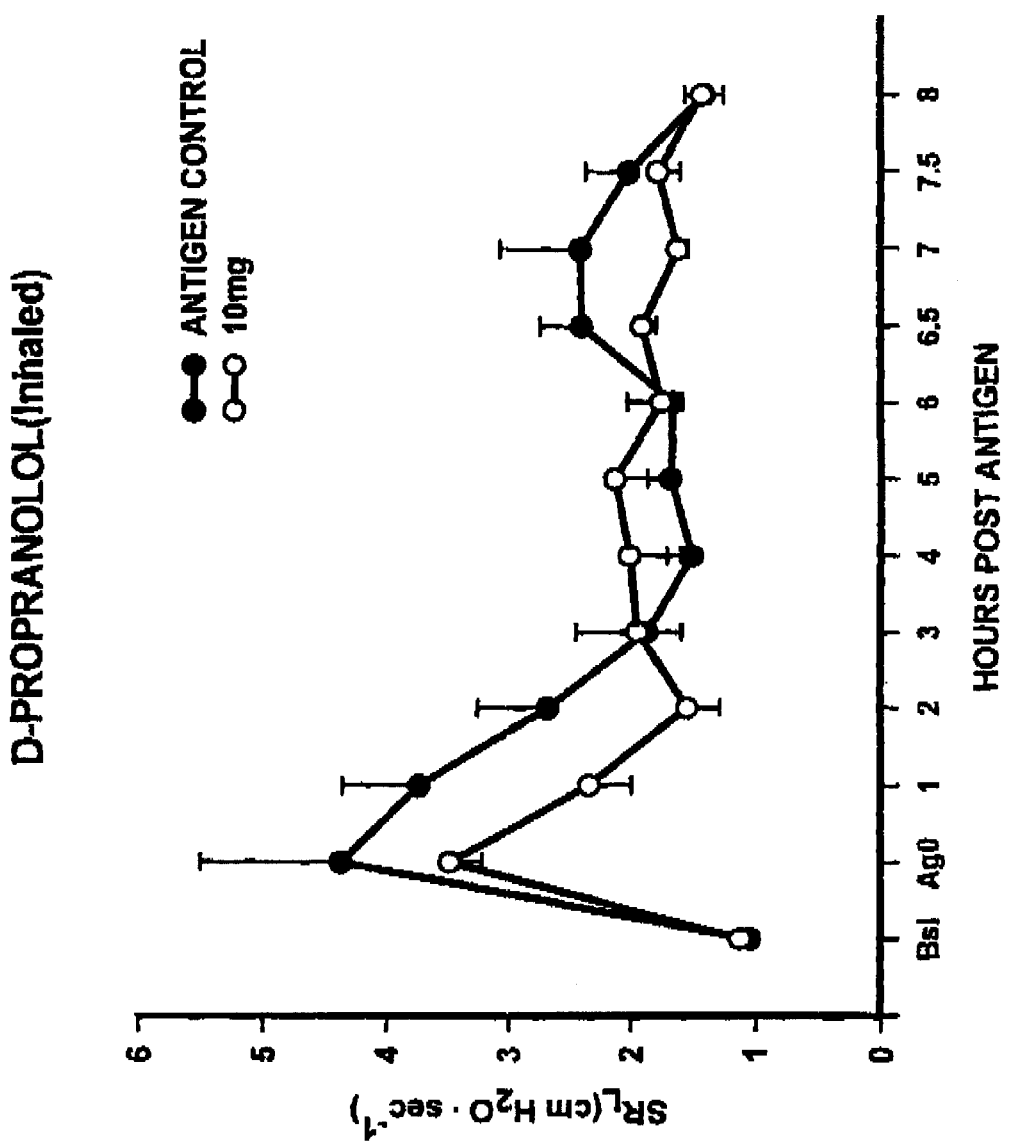
FIG. 14 is a chart showing the timeline of the $SR_L$ response of dual responder sheep to a 10 mg/kg dose of inhaled D-propranolol.
Figure 15:
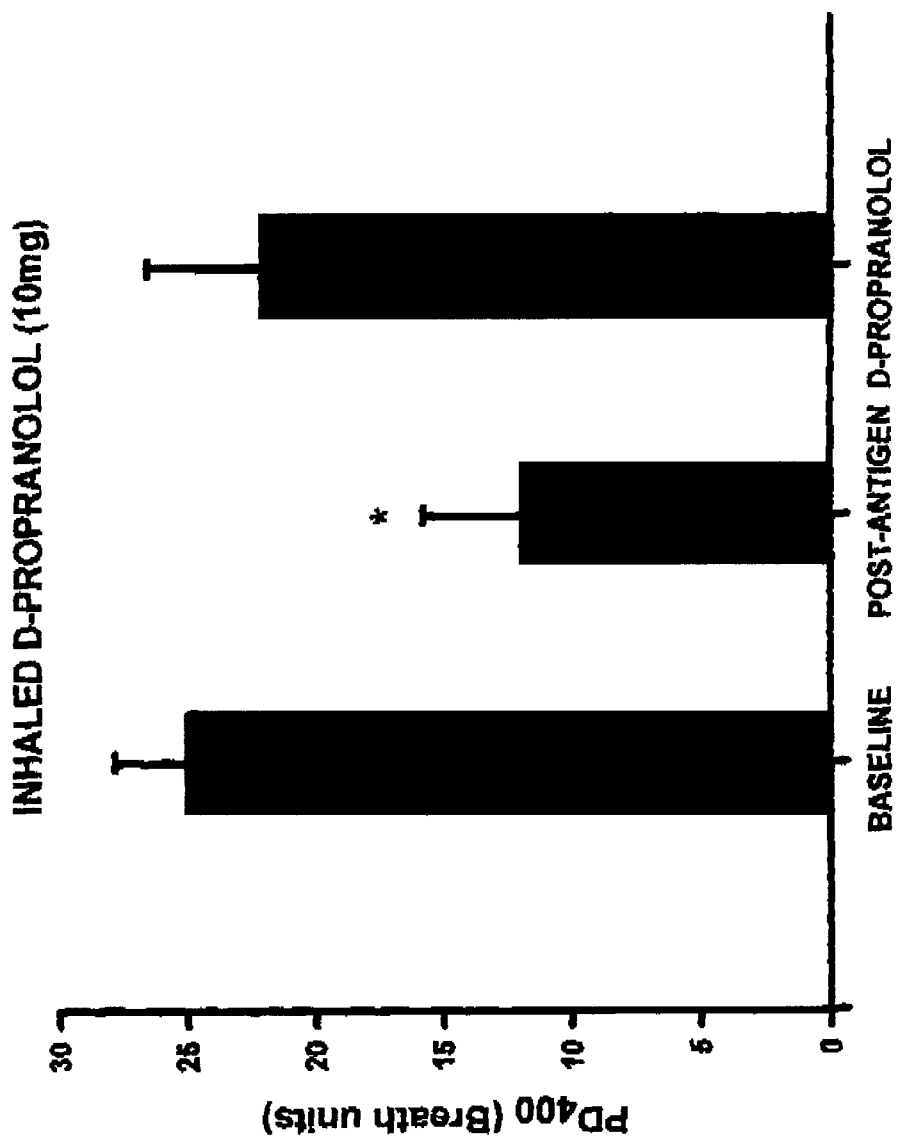
FIG. 15 is a graph showing the $PD_{400}$ response of dual responder sheep to a 10 mg/kg dose of inhaled D-propranolol.
Figure 18:
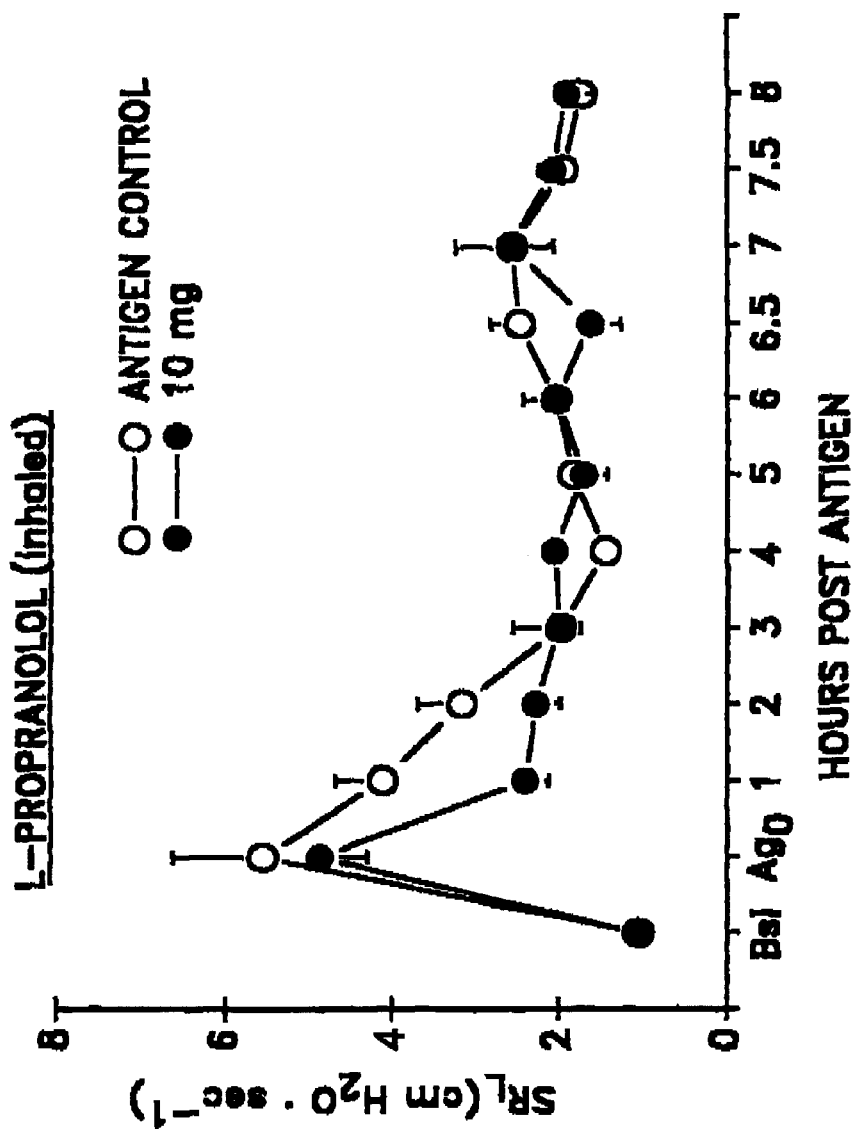
FIG. 18 is a chart showing the timeline of the $SR_L$ response of dual responder sheep to a 10 mg/kg dose of inhaled L-propranolol.
Figure 19:
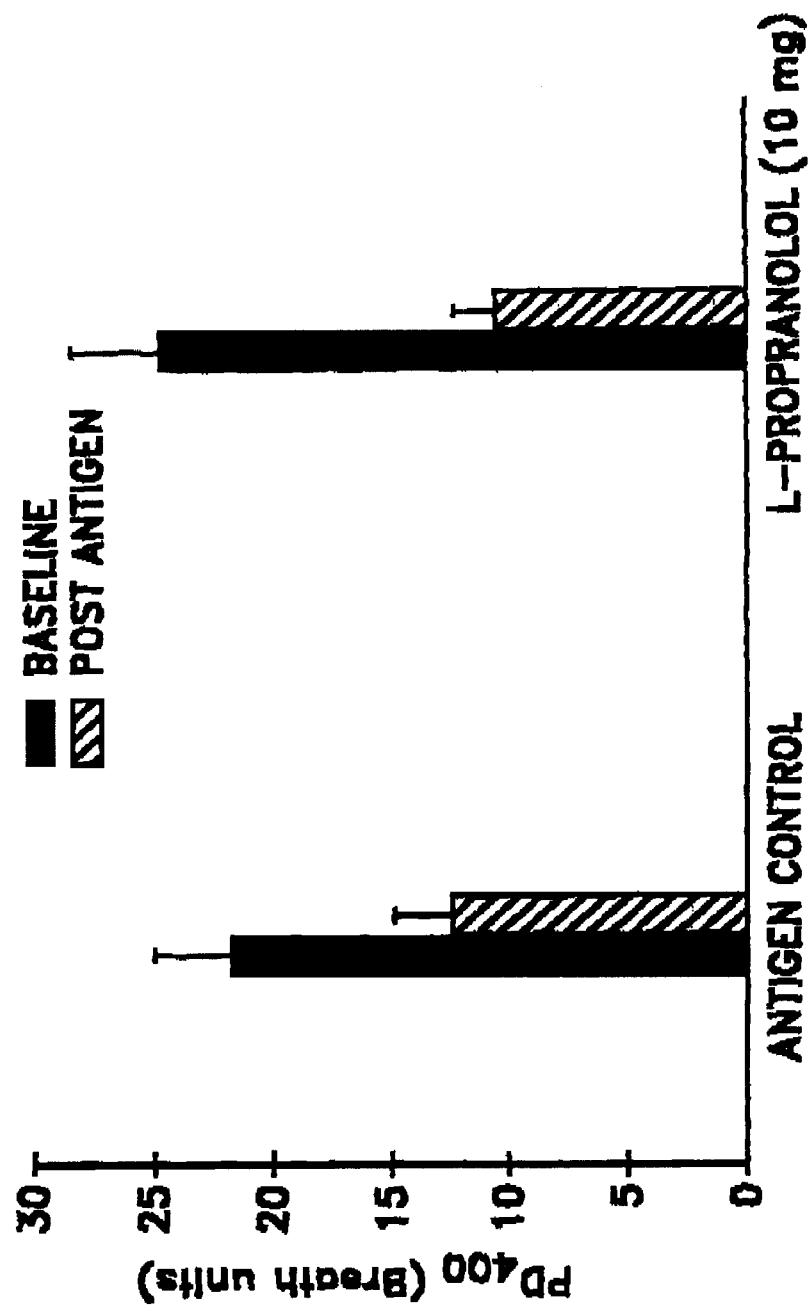
FIG. 19 is a graph showing the $PD_{400}$ response of dual responder sheep to a 10 mg/kg dose of inhaled L-propranolol.

In dual responders, L-propranolol was ineffective, with peak early change in $SR_L$=351%, peak late $SR_L$=175%, as shown in FIG. 18, and had no effect on $PD_{400}$ as shown in FIG. 19. With D-propranolol, at a 5 mg dose, partly attenuated the early phase and late phase by 35% and 21%, respectively, and inhibited AHR by 44% (P<0.05), as shown in FIGS. 12 and 13. Inhaled D-propranolol at a 10 mg dose also effected ABR, see FIG. 14, and AHR, see FIG. 15.

Figure 16:
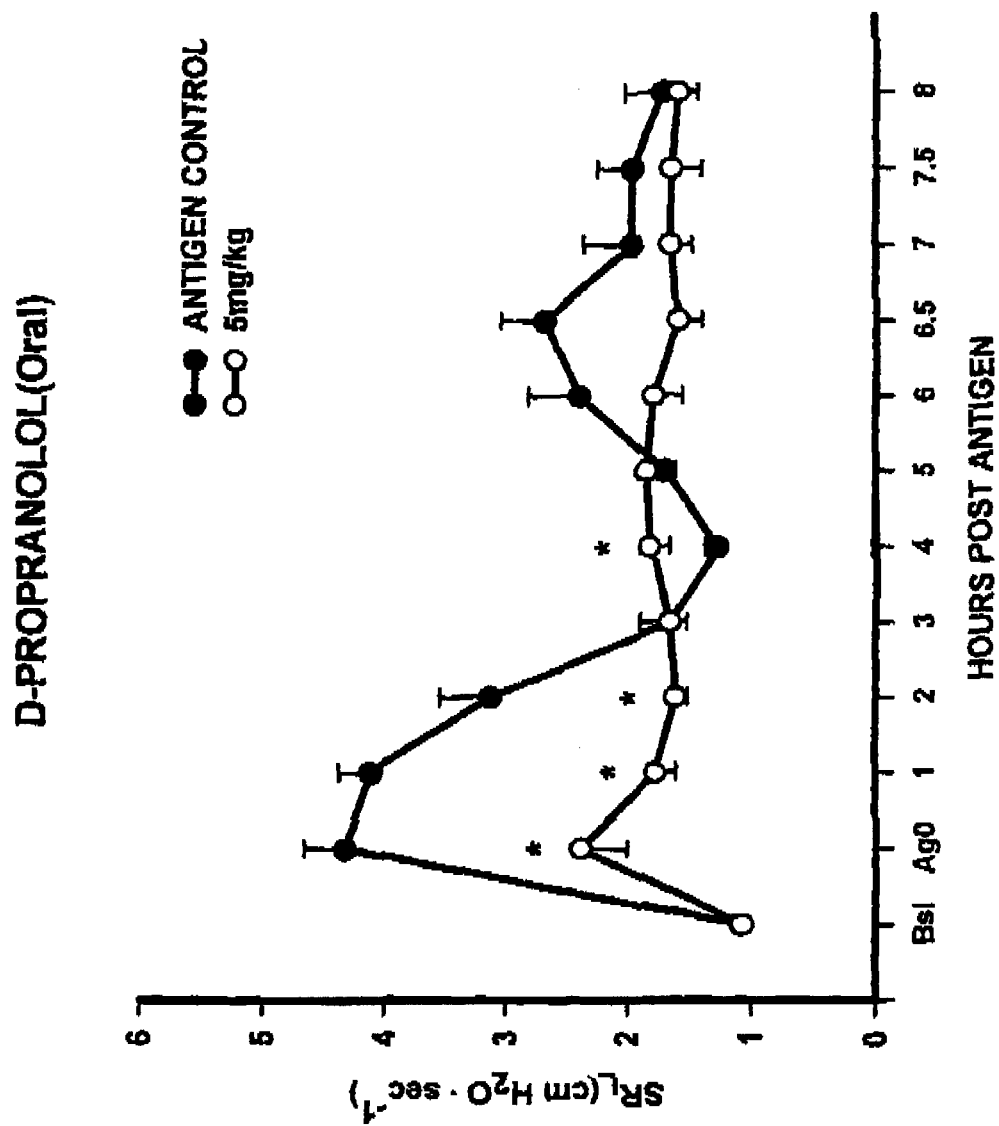
FIG. 16 is a chart showing the timeline of the $SR_L$ response of dual responder sheep to a 5 mg/kg dose of oral D-propranolol.
Figure 17:
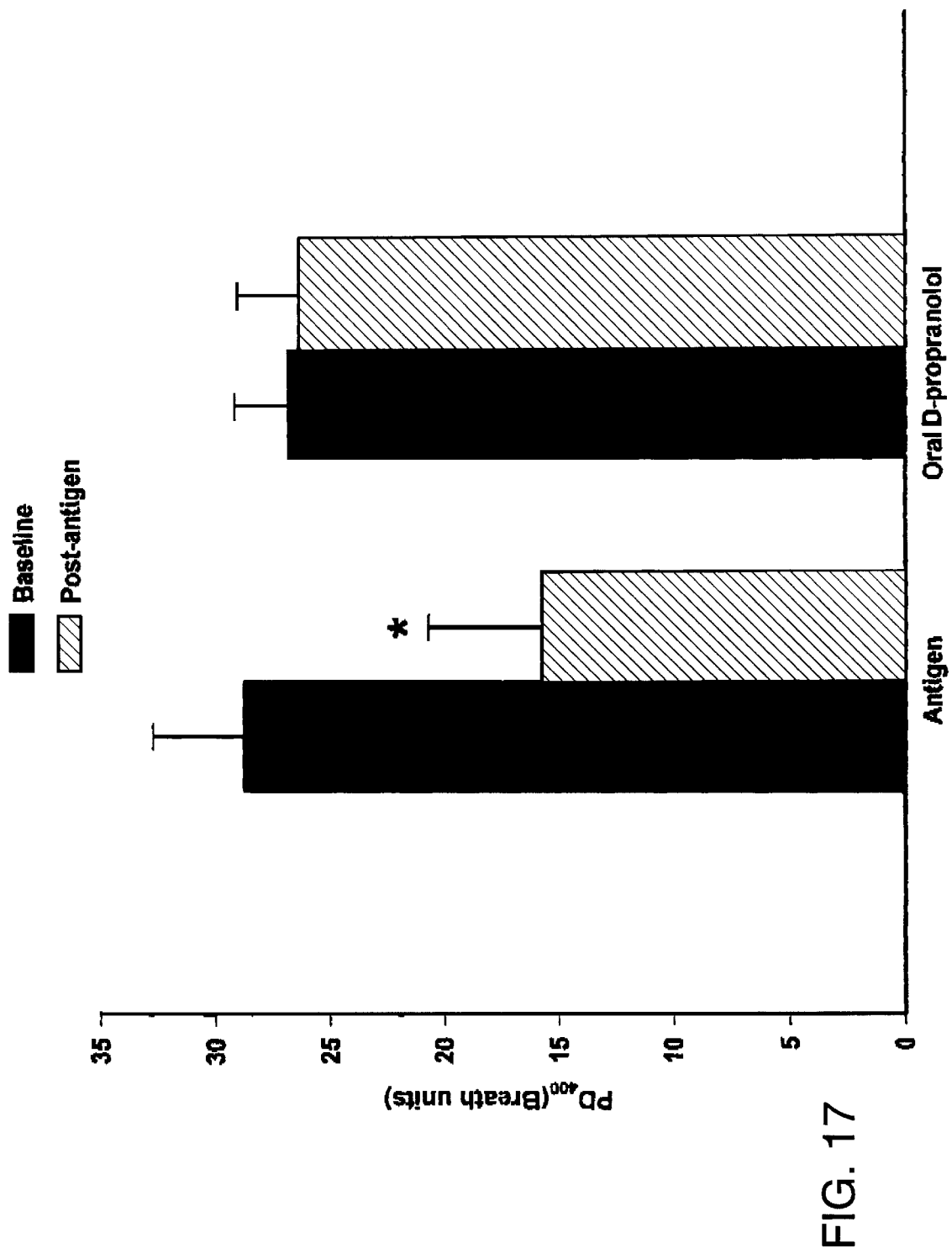
FIG. 17 is a graph showing the $PD_{400}$ response of dual responder sheep to a 5 mg/kg dose of oral D-propranolol.

The route of administration was not critical in the effect of D-propranolol on ABR and AHR. As shown in FIG. 16, oral administration of 5 mg/kg of D-propranolol significantly effected the early phase of dual responder sheep, and may even remove the late phase response. A 5 mg/kg oral dose also effected AHR as shown in FIG. 17.

It should be understood, of course, that the foregoing relates only to preferred embodiments of the present invention and that numerous modifications or alterations may be made therein without departing from the spirit and the scope of the invention as set forth in the appended claims.

What is claimed is:

1. A method of treatment of bronchorestriction in a human or animal, comprising administering an effective amount of a drug selected from the group consisting of D-propranolol, metoprolol, carvedilol, and bisoprolol and congeners and analogs, and metabolites thereof, to inhibit bronchorestriction in the human or animal.

2. The method of claim 1, wherein the bronchorestriction is asthma.

3. The method of claim 1, wherein the bronchorestriction is bronchial hyperresponsiveness.

\* \* \* \* \*